(12) United States Patent
Klautky et al.

(10) Patent No.: US 7,803,624 B2
(45) Date of Patent: Sep. 28, 2010

(54) AUTOMATED CYTOLOGICAL SAMPLE CLASSIFICATION

(75) Inventors: Trudee Klautky, Shrewsbury, MA (US); Daniel Lapen, Lancaster, MA (US)

(73) Assignee: CYTYC Corporation, Marlborough, MA (US)

( * ) Notice: Subject to any disclaimer, the term of this patent is extended or adjusted under 35 U.S.C. 154(b) by 1541 days.

(21) Appl. No.: 10/676,568

(22) Filed: Sep. 30, 2003

(65) Prior Publication Data

US 2005/0070020 A1 Mar. 31, 2005

(51) Int. Cl.
*G01N 30/04* (2006.01)

(52) U.S. Cl. .......................... 436/10; 436/50; 436/164; 436/165; 436/180; 422/73; 356/36

(58) Field of Classification Search .................. 436/10, 436/50, 164, 165, 180; 422/73; 356/36
See application file for complete search history.

(56) References Cited

U.S. PATENT DOCUMENTS

| | | | | |
|---|---|---|---|---|
| 3,827,805 | A * | 8/1974 | Mansfield et al. | 356/73 |
| 4,129,381 | A * | 12/1978 | Wied et al. | 356/36 |
| 5,168,066 | A * | 12/1992 | Zahniser et al. | 436/63 |
| 5,256,571 | A | 10/1993 | Hurley et al. | |
| 5,266,495 | A * | 11/1993 | Lapidus | 436/63 |
| 5,690,893 | A | 11/1997 | Ozawa et al. | |
| 6,025,485 | A | 2/2000 | Kamb et al. | |
| 6,258,340 | B1 | 7/2001 | Licha et al. | |
| 6,329,167 | B1 | 12/2001 | Patterson | |
| 6,566,057 | B1 | 5/2003 | Kamb et al. | |
| 6,629,057 | B2 * | 9/2003 | Zweig et al. | 702/182 |
| 2002/0094577 | A1 | 7/2002 | Guirguis et al. | |
| 2002/0150285 | A1 | 10/2002 | Nelson | |
| 2002/0198928 | A1 * | 12/2002 | Bukshpan et al. | 709/200 |
| 2004/0253144 | A1 * | 12/2004 | Isenstein et al. | 422/61 |

FOREIGN PATENT DOCUMENTS

| | | |
|---|---|---|
| CN | 1115851 | 1/1996 |
| EP | 0735358 | 10/1996 |
| EP | 632 895 B1 | 7/1998 |
| EP | 455 757 B1 | 3/1999 |
| EP | 573 535 B1 | 12/2000 |
| EP | 1 019 687 B1 | 1/2002 |
| EP | 988 525 B1 | 4/2002 |
| WO | WO96/00892 | 1/1996 |
| WO | 0194016 | 12/2001 |
| WO | 0244691 | 6/2002 |

OTHER PUBLICATIONS

G. Bou-Habib, et al "Use of At-Line Spectrophometry for the Rapid Definition of Pilot-Scale Flocculation Processes" Americant Chemical Society and American Institute of Chemical Engineers Published on Web Feb. 23, 2002; Biotechnol. Prog 2002, 18, 387-393.

Hisako Shibata, et al "Automatic Analisys of Normal Bone Marrow Blood Cells Using the XE-2100 Automated Hematology Analyzer" Journal of Clinical Laboratory Analysis 17:12-17 (2003).

C. S. Scott, et al "Automated Detection of Malaria-Associated Intraleucocytic Haemozoln by Cell-Dyn CD4000 Depolarization Analysis" Clin. Lab. Haem. 2003, 25, 77-86.

Jurgen Eichler, et al "Nonlinear Scattering in Hard Tissue Studied with Ultrashort Laser Pulses" Z. Med, Phys. 12 (2002) 191-197.

Business Communications, "Preliminary Color Test & Serological Characterization of Semen", MarkIntel Business Communications, Sep. 30, 1999.

PCT International Search Report for PCT/US04/31441, Applicant: Cytyc Corporation, Form PCT/ISA/210, dated Mar. 24, 2006 (2 pages).

PCT Written Opinon of the International Searching Authority for PCT/US04/31441, Applicant. Cytyc Corporation, Form PCT/ISA/237) dated Mar. 24, 2006 (4 pages).

First Office Action dated Mar. 7, 2008 for Chinese Application No. 200480028155.0, Applicant: Cytyc Corporation (10 pages).

European Search Report for PCT/US2004/031441 (04785004.5-1234), Applicant Cytyc Corporation, dated Oct. 17, 2008, EPO Form 1507.4, 1503 02.82, 1503 03.82, P0459 (5 pages).

Examiner's First report for related Australian application No. 2004278730, dated Aug. 6, 2008, Applicant Cytyc Corporation, (3 pages).

Response to Examiner's First report for related Australian application No. 2004278730, dated Aug. 6, 2008, Applicant Cytyc Corporation, response submitted on Oct. 6, 2008 (11 pages).

Examiner's Second report for related Australian application 2004278730, dated Oct. 28, 2008, Applicant Cytyc Corporation, (2 pages).

Response to Examiner's Second report for related Australian application No. 2004278730, dated Oct. 28, 2008, Applicant Cytyc Corporation, response submitted on Mar. 17, 2009 (13 pages).

Examiner's Third report for related Australian application 2004278730, dated Mar. 25, 2009, Applicant Cytyc Corporation, (1 page).

* cited by examiner

*Primary Examiner*—Lyle A Alexander
(74) *Attorney, Agent, or Firm*—Vista IP Law Group LLP

(57) ABSTRACT

An automated method for classifying a cytological sample is provided. The method comprises interrogating the sample with one or more wavelengths of light to obtain a result, and then attaching one or more designators to the sample based on whether the result meets a given criterion. The method allows for rapid feedback on the characteristics of the sample, permitting automated designation of the sample as positive for a given characteristic, and allowing for immediate remedial actions if the sample fails to meet the criterion.

16 Claims, No Drawings

AUTOMATED CYTOLOGICAL SAMPLE CLASSIFICATION

TECHNICAL FIELD

This invention relates to automated methods for classifying cytological samples.

BACKGROUND OF THE INVENTION

Modern diagnostic techniques have provided highly sensitive tools capable of unprecedented informational capacity and throughput. Many techniques, such as the Papanicolaou staining method, have been well adapted to automated processes, which has further improved their consistency and reliability.

However, diagnostic techniques still suffer from age-old limitations in sample collection and patient compliance. Sampling processes, especially those which are difficult, highly invasive and/or painful, frequently result in inadequate specimens. Typically there is a delay between the time the sample is obtained and the time when the adequacy of the sample is determined, during which the patient has left the point of sampling. Upon learning that the sample is inadequate, the patient is presented with additional inconvenience, pain and recovery from a second sampling procedure. This frequently leads to missed resampling appointments. The danger of this is acute, particularly in younger patients who may have significant barriers to subjecting themselves to medical treatment. Often such younger patients are the very ones most likely to be exposed to sexually transmitted diseases, yet are the least likely to return should their original sample prove inadequate. Indeed, it may be difficult or impossible to contact patients who originally were tested in a confidential or anonymous setting.

Consequently, there is a need for a method for quickly determining cytological sample adequacy.

SUMMARY OF THE INVENTION

An automated method for classifying a cytological sample is provided. The method comprises interrogating the sample with one or more wavelengths of light to obtain a result, and then attaching one or more designators to the sample based on whether the result meets a given criterion. The method allows for rapid feedback on the characteristics of the sample, permitting automated designation of the sample as positive for a given characteristic, and allowing for immediate remedial actions if the sample fails to meet the criterion.

DETAILED DESCRIPTION OF THE INVENTION

An automated method of classifying a cytological sample is provided. The method comprises interrogating the sample with at least one wavelength of light to obtain a result indicative of a characteristic of the sample. That result is compared to a criterion suitable for distinguishing samples that meet a given criterion. A designator is then attached to the sample reflecting whether or not it meets the criterion. The automated designation system permits the rapid determination of sample adequacy for particular assays. The method can be used in conjunction with molecularly-based methods of interrogating the sample for particular biomolecules.

Before the present invention is described in further detail, it is to be understood that this invention is not limited to the particular methodology, solutions or apparatuses described, as such methods, solutions or apparatuses can, of course, vary. It is also to be understood that the terminology used herein is for the purpose of describing particular embodiments only, and is not intended to limit the scope of the present invention.

Use of the singular forms "a," "an," and "the" include plural references unless the context clearly dictates otherwise. Thus, for example, reference to "a designator" includes a plurality of designators, reference to "a wavelength" includes a plurality of wavelengths, reference to "a target" includes a plurality of targets, and the like. Additionally, use of specific plural references, such as "two," "three," etc., read on larger numbers of the same subject unless the context clearly dictates otherwise.

Terms such as "connected," "attached," and "linked" are used interchangeably herein and encompass direct as well as indirect connection, attachment, linkage or conjugation unless the context clearly dictates otherwise. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. Where a value being discussed has inherent limits, for example where a component can be present at a concentration of from 0 to 100%, or where the pH of an aqueous solution can range from 1 to 14, those inherent limits are specifically disclosed. Where a value is explicitly recited, it is to be understood that values which are about the same quantity or amount as the recited value are also within the scope of the invention, as are ranges based thereon. Where a combination is disclosed, each subcombination of the elements of that combination is also specifically disclosed and is within the scope of the invention. Conversely, where different elements or groups of elements are disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

Unless defined otherwise or the context clearly dictates otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

All publications mentioned herein are hereby incorporated by reference for the purpose of disclosing and describing the particular materials and methodologies for which the reference was cited. The publications discussed herein are provided solely for their disclosure prior to the filing date of the present application. Nothing herein is to be construed as an admission that the invention is not entitled to antedate such disclosure by virtue of prior invention.

The terms "polynucleotide," "oligonucleotide," "nucleic acid" and "nucleic acid molecule" are used interchangeably herein to refer to a polymeric form of nucleotides of any length, and may comprise ribonucleotides, deoxyribonucleotides, analogs thereof, or mixtures thereof. These terms refer only to the primary structure of the molecule. Thus, the terms includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide.

Suitable hybridization conditions for a given assay format can be determined by one of skill in the art; nonlimiting parameters which may be adjusted include concentrations of assay components, pH, salts used and their concentration, ionic strength, temperature, etc.

More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, hRNA, and mRNA, whether spliced or unspliced, any other type of polynucleotide which is an N- or C-glycoside of a purine or pyrimidine base, and other polymers containing alternative backbones, including peptide nucleic acid (PNA), and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms are used interchangeably herein. These terms refer only to the primary structure of the molecule. Thus, these terms include, for example, 3'-deoxy-2',5'-DNA, oligodeoxyribonucleotide 3' P5' phosphoramidates, 2'-O-alkyl-substituted RNA, double- and single-stranded DNA, as well as double- and single-stranded RNA, and hybrids thereof including for example hybrids between DNA and/or RNA and/or PNA and/or other forms, and also include known types of modifications, for example, labels, alkylation, "caps," substitution of one or more of the nucleotides with an analog, internucleotide modifications such as, for example, those with negatively charged linkages (e.g., phosphorothioates, phosphorodithioates, etc.), those containing pendant moieties, such as, for example, proteins (including enzymes (e.g. nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, e.g., wherein one or more of the hydroxyl groups are replaced with halogen, aliphatic groups, or are functionalized as ethers, amines, or the like. The term "nucleotidic unit" is intended to encompass nucleosides and nucleotides.

Furthermore, modifications to nucleotidic units include rearranging, appending, substituting for or otherwise altering functional groups on the purine or pyrimidine base which form hydrogen bonds to a respective complementary pyrimidine or purine. The resultant modified nucleotidic unit optionally may form a base pair with other such modified nucleotidic units but not with A, T, C, G or U. Abasic sites may be incorporated which do not prevent the function of the polynucleotide; preferably the polynucleotide does not comprise abasic sites. Some or all of the residues in the polynucleotide can optionally be modified in one or more ways.

"Complementary" or "substantially complementary" refers to the ability to hybridize or base pair between nucleotides or nucleic acids, such as, for instance, between a sensor peptide nucleic acid and a target polynucleotide. Complementary nucleotides are, generally, A and T (or A and U), or C and G. Two single-stranded polynucleotides or PNAs are said to be substantially complementary when the bases of one strand, optimally aligned and compared and with appropriate insertions or deletions, pair with at least about 80% of the bases of the other strand, usually at least about 90% to 95%, and more preferably from about 98 to 100%.

Alternatively, substantial complementarity exists when a polynucleotide or PNA will hybridize under selective hybridization conditions to its complement. Typically, selective hybridization will occur when there is at least about 65% complementary over a stretch of at least 14 to 25 bases, preferably at least about 75%, more preferably at least about 90% complementary. See, M. Kanehisa Nucleic Acids Res. 12:203 (1984).

"Preferential binding" or "preferential hybridization" refers to the increased propensity of one polynucleotide or PNA to bind to its complement in a sample as compared to a noncomplementary polymer in the sample.

Hybridization conditions will typically include salt concentrations of less than about 1M, more usually less than about 500 mM and preferably less than about 200 mM. In the case of hybridization between a peptide nucleic acid or other similar nucleic acid and a polynucleotide, the hybridization can be done in solutions containing little or no salt. Hybridization temperatures can be as low as 5° C., but are typically greater than 22° C., more typically greater than about 30° C., and preferably in excess of about 37° C. Longer fragments may require higher hybridization temperatures for specific hybridization. Other factors may affect the stringency of hybridization, including base composition and length of the complementary strands, presence of organic solvents and extent of base mismatching, and the combination of parameters used is more important than the absolute measure of any one alone. Other hybridization conditions which may be controlled include buffer type and concentration, solution pH, presence and concentration of blocking reagents to decrease background binding such as repeat sequences or blocking protein solutions, detergent type(s) and concentrations, molecules such as polymers which increase the relative concentration of the polynucleotides, metal ion(s) and their concentration(s), chelator(s) and their concentrations, and other conditions known in the art.

The terms "aptamer" (or "nucleic acid antibody") is used herein to refer to a single- or double-stranded polynucleotide that recognizes and binds to a desired target molecule by virtue of its shape. See, e.g., PCT Publication Nos. WO 92/14843, WO 91/19813, and WO 92/05285.

"Polypeptide" and "protein" are used interchangeably herein and include a molecular chain of amino acids linked through peptide bonds. The terms do not refer to a specific length of the product. Thus, "peptides," "oligopeptides," and "proteins" are included within the definition of polypeptide. The terms include polypeptides contain [post-translational] modifications of the polypeptide, for example, glycosylations, acetylations, phosphorylations, and sulphations. In addition, protein fragments, analogs (including amino acids not encoded by the genetic code, e.g. homocysteine, ornithine, D-amino acids, and creatine), natural or artificial mutants or variants or combinations thereof, fusion proteins, derivatized residues (e.g. alkylation of amine groups, acetylations or esterifications of carboxyl groups) and the like are included within the meaning of polypeptide.

As used herein, the term "binding pair" refers to first and second molecules that bind specifically to each other with greater affinity than to other components in the sample. The binding between the members of the binding pair is typically noncovalent. Exemplary binding pairs include immunological binding pairs (e.g. any haptenic or antigenic compound in combination with a corresponding antibody or binding portion or fragment thereof, for example digoxigenin and anti-digoxigenin, fluorescein and anti-fluorescein, dinitrophenol and anti-dinitrophenol, bromodeoxyuridine and anti-bromodeoxyuridine, mouse immunoglobulin and goat anti-mouse immunoglobulin) and nonimmunological binding pairs (e.g., biotin-avidin, biotin-streptavidin, hormone [e.g., thyroxine and cortisol]-hormone binding protein, receptor-receptor agonist or antagonist (e.g., acetylcholine receptor-acetylcholine or an analog thereof), IgG-protein A, lectin-carbohydrate, enzyme-enzyme cofactor, enzyme-enzyme-inhibitor, and complementary polynucleotide pairs capable of forming nucleic acid duplexes) and the like. One or both member of the binding pair can be conjugated to additional molecules.

The term "antibody" as used herein includes antibodies obtained from both polyclonal and monoclonal preparations, as well as: hybrid (chimeric) antibody molecules (see, for example, Winter et al. (1991) Nature 349:293-299; and U.S. Pat. No. 4,816,567); F(ab')$_2$ and F(ab) fragments; Fv molecules (noncovalent heterodimers, see, for example, Inbar et al. (1972) Proc Natl Acad Sci USA 69:2659-2662; and Ehrlich et al. (1980) Biochem 19:4091-4096); single-chain Fv molecules (sFv) (see, for example, Huston et al. (1988) Proc Natl Acad Sci USA 85:5879-5883); dimeric and trimeric antibody fragment constructs; minibodies (see, e.g., Pack et al. (1992) Biochem 31:1579-1584; Cumber et al. (1992) J Immunology 149B:120-126); humanized antibody molecules (see, for example, Riechmann et al. (1988) Nature 332:323-327; Verhoeyan et al. (1988) Science 239:1534-1536; and U.K. Patent Publication No. GB 2,276,169, published 21 Sep. 1994); and, any functional fragments obtained from such molecules, wherein such fragments retain specific-binding properties of the parent antibody molecule.

As used herein, the term "monoclonal antibody" refers to an antibody composition having a homogeneous antibody population. The term is not limited regarding the species or source of the antibody, nor is it intended to be limited by the manner in which it is made. Thus, the term encompasses antibodies obtained from murine hybridomas, as well as human monoclonal antibodies obtained using human hybridomas or from murine hybridomas made from mice expression human immunoglobulin chain genes or portions thereof. See, e.g., Cote, et al. Monoclonal Antibodies and Cancer Therapy, Alan R. Liss, 1985, p. 77.

"Multiplexing" herein refers to an assay or other analytical method in which multiple analytes can be assayed simultaneously.

"Optional" or "optionally" means that the subsequently described event or circumstance may or may not occur, and that the description includes instances where the event or circumstance occurs and instances in which it does not.

The automated method of sample classification can be performed on a cytological sample that can be obtained in any manner. Suitable techniques are known in the art. The sample can be any source of biological material that can be obtained from a living organism directly or indirectly, including cells, tissue or fluid. Nonlimiting examples of the sample include blood, urine, semen, milk, sputum, mucus, pleural fluid, pelvic fluid, sinovial fluid, ascites fluid, body cavity washes, eye brushing, skin scrapings, a buccal swab, a vaginal swab, a pap smear, a rectal swab, an aspirate, a needle biopsy, a section of tissue obtained for example by surgery or autopsy, plasma, serum, spinal fluid, lymph fluid, the external secretions of the skin, respiratory, intestinal, and genitourinary tracts, tears, saliva, tumors, organs, a microbial culture, a virus, and samples of in vitro cell culture constituents.

The sample can be collected or placed in a solution used for liquid based cytology or a medium that lyses the cells and dissolves a portion or all of the molecular components into solution. In one embodiment, the sample may comprise a preservative solution such as PreservCyt® Solution (Cytyc Corp.).

The sample can comprise a preservative solution suitable for preservation of cells and tissue at ambient temperatures. The solution can comprise an alcohol and preferably a buffer, and can be used for in vitro preservation of mammalian cells at ambient temperatures following biopsy, and prior to staining or other forms of analysis. The solution can be one such as described in U.S. Pat. No. 5,256,571 to Hurley et al. issued Oct. 26, 1993. The preservative solution can comprise a water-miscible alcohol, and preferably an anti-clumping agent and a buffering agent. The alcohol constituent is present in an amount sufficient to fix sample cells or tissue while still permitting acceptable binding of the sensor to its target. The alcohol is typically a lower alkyl ($C_{1-6}$) alcohol, and may be a $C_{1-4}$ alcohol, and may be selected from the group consisting of methanol, ethanol and isopropanol. The alcohol may be present in an amount greater than about 40% and less than about 60%, and may be about 45% or more, and may be about 55% or less. In another variation, the alcohol is present in an amount of at least approximately 20 percent by solution. The anti-clumping agent may be present in an amount sufficient to prevent cells from clumping in solution. Any suitable anti-clumping agent effect in the alcoholic preservative solution can be used, and can be, for example, a chelating agent selected, for example, from the group consisting of ethylenediaminetetraacetic acid (EDTA), and its salts, such as disodium, tripotassium and tetrasodium. Other agents deemed useful as the anti-clumping agent include cuminin, heparin, streptokinase, and such agents found in lysing or anticoagulant compositions. Any buffering agent which can maintain the preservative solution at a desired pH during use may be used. Exemplary buffering agents include PBS, Tris, sodium acetate, and citric acid. EDTA and its salts may also be used as a buffering agent. The buffering agent can be one which maintains the pH of the solution within a range of between about four to about seven for the duration of preservation. Accordingly, a preferred buffer is an acetate buffer, such as sodium acetate, magnesium acetate, calcium acetate, and combinations thereof. A detergent may also be used in the solution. The detergent may be non-ionic, cationic, anionic or zwitterionic. Mixtures of detergents may also be used. Exemplary classes of detergents include alcohol ether sulfates, alcohol sulfates, alkanolamides, alkyl sulfonates, amine oxides, amphoteric detergents, anionic detergents, betaine derivatives, cationic detergents, disulfonates, dodecylbenzene sulfonic acid, ethoxylated alcohols, ethoxylated alkyl phenols, ethoxylated fatty acids, glycerol esters hydrotropes, lauryl sulfates, mono and diglycerides, non-ionic detergents, phosphate esters, quaternary detergents, and sorbitan derivatives.

Automation classification of the sample is a key feature of the invention. This permits the healthcare provider or laboratory technician to rapidly determine whether a sample meets a given criterion, allowing for example the performance of additional diagnostic tests on the sample without compromising an intended assay, for example a Papanicolaou staining procedure or a variant thereof. The automated method also allows remedial action to be taken should the sample not meet the criterion.

The sample is provided for automated analysis in a vessel; suitable vessels are known in the art. The vessel can be any vessel capable of retaining a cytological sample that is a solution, and permits optically interrogation of the solution to determine its adequacy for one or more criteria. The vessel can be sealable, and may be a cellular vial such as those suitable for use with the ThinPrep® 2000 Processor (Cytyc Corp.). One or more surfaces of the vessel and/or any attachments (e.g., a cap) are sufficiently transparent to the light used to interrogate the sample that the result can be determined.

The sample may be classified for a plurality of different criteria using different interrogation methods. The sample may be interrogated using different wavelengths of light, different optical techniques, and combinations thereof. The sample may be interrogated for absorbance, transmittance, fluorescence, scattering, etc., and combinations thereof. The sample may be mixed prior to interrogation, and the mixing may be performed manually or automatically; the apparatus may incorporate a mixing capability to perform this function.

The sample may be interrogated with any of a variety of wavelengths of light, including ultraviolet, visible, infrared, near infrared, mid infrared, far infrared, ultraviolet, near ultraviolet, far ultraviolet, extreme ultraviolet, UV-A, and UV-B. The light source, in combination with optional filter(s), may provide one or more precise wavelengths of light, may provide ranges of wavelengths, or combinations of any thereof, and more than one different light source can be used. Any light source capable of producing a wavelength useful for interrogating the sample regarding a criterion of interest may be used; a plurality of light sources can be used in such an automated apparatus. Exemplary light sources include: an infrared lamp, for example a lamp with a filament consisting of wound Kanthal or Nichrome optionally linked with a sapphire, zinc selenide or calcium fluoride transmission window, a heat lamp, a light emitting diode, a fiber optic source, a visible lamp, a pulsed visible lamp, a deuterium lamp; a xenon lamp; a continuous wave (cw) gas laser, including but not limited to any of the Argon Ion laser lines (457, 488, 514, etc. nm) or a HeCd laser; a solid state diode laser such as a GaN and GaAs (doubled) based laser or the doubled or tripled output of YAG or YLF based lasers; and a pulsed laser.

A result obtained from interrogating the sample is compared to a criterion. The criterion is set to permit satisfactory classification of the sample based on the result of the interrogation. The criterion may be an absorbance, a transmittance, a reflectance, a degree of scattering, a luminescence, a fluorescence, an emission, or backscattering, and may be at a particular wavelength or selection of wavelengths. The criterion may be an absolute number, and may be stored in any manner by the device, including in software, in a fixed memory, and/or in a programmable memory. The criterion may be a relative value which is obtained upon comparison to one or more control samples by the apparatus. The criterion may be a minimum threshold or a maximum threshold. A plurality of different criterion may be used for classifying the sample in a plurality of different ways, and may be applied simultaneously, sequentially, or in combinations thereof. For example, the criterion may be an absorbance at a particular wavelength of light. The criterion may be selective for a specific cell type, for example endocervical cells, whose presence in a pap smear sample is indicative of sampling of the cervix. To determine the number or concentration of cells in a sample, an absorbance at a particular wavelength of light can be used; a suitable wavelength, for example in the visible or infrared, can be determined empirically by comparing the absorption spectrum of the solution in which the sample is to be suspended in the presence and absence of cells. Particular sample components, for example particular cell types, can be detected by any suitable means, for example by using a competitive assay such as a binding pair with one member linked to a fluorophore and the other to a quencher; competition for binding to one member of the binding pair releases the fluorophore from the quencher, thereby providing a fluorescent signal which can be detected. This can be done with an antibody specific for an antigen present on a cell type of interest. Mucus can be detected using a competitive assay using fluorescently labeled wheat germ agglutinin (Oregon Green or tetramethyl rhodamine; Molecular Probes), a lectin that specifically binds to N-acetylneuraminic acid (sialic acid) residues present in mucus. The presence of blood in the sample can be detected, for example, at a wavelength of 405-420 nm.

Comparison of the result obtained from the optical interrogation results in the automated attachment of a designator to the sample. The sample can be a positive designator or a manipulation designator. The positive designator indicates that the sample meets the criterion. For example, the positive designator may indicate that a sufficient number of cells, which may be of a select type, are present in the sample. The positive designator may indicate that sufficient cells are present in the sample to permit performance of additional methods on the sample beyond an intended method for which the sample was designated; for example, the positive example may indicate that withdrawal of an aliquot of the sample for molecular testing may be performed prior subjecting the sample to automated slide preparation. This is extremely desirable because automated methods are considered susceptible to cross-contamination from sample to sample, and therefore withdrawal of the remaining sample from a vial which has already been subjected to automated processing is considered unreliable. Cytologists would prefer that sample adequacy be determined prior to automated sample preparation so that an uncontaminated sample could be removed and subjected to other tests, such as molecular HPV (human papilloma virus) tests.

The manipulation designator indicates that the sample must be subjected to a manipulation to render it adequate for an intended test. For example, the manipulation designator may indicate that sufficient cells, or sufficient cells of a particular type, are not present in the sample, and thus can designate the acquisition of additional sample. The manipulation designator may indicate that the sample must be treated to render it acceptable. For example, where the sample contains excessive blood and fails to meet a criterion for a satisfactory blood level, a manipulation designator may be attached to the sample indicating that a pre-treatment step be performed. The pretreatment step may be an acetic acid treatment. Where the sample contains excessive mucus, a manipulation designator may be assigned, for example to acquire another sample, or to treat the sample with a mucus-reducing agent, e.g. a reducing agent such as dithiothreitol. The manipulation designator may indicate other treatments, such as filtration of the sample, or washing of the sample.

The designators may be attached to the sample in any manner, may be physically attached, electronically attached, and attached in multiple ways. Physical attachment can be accomplished, for example, by placing a marking on the sample vessel, or by attaching a label reflecting the designation to the sample vessel. An apparatus may incorporate a printing, engraving, etching or other apparatus for marking the vessel directly, and may incorporate a label printer or label attachment device for attaching a label to the vessel. The designator may be electronically attached to the vessel, for example in an electronic memory, which may be attached to the vessel by correlation to a sample number, a sample position, or a code or other designation on the sample vessel.

The methods can thus be performed in conjunction with sample collection, providing distinct advantages. The particular methods can be performed in a healthcare setting, allowing for determination of sample adequacy prior to the patient leaving the healthcare facility, and may be done at the point of sampling allowing for performance of the methods in temporal conjunction with obtaining the sampling. Thus additional sample can be obtained at that time, rather than requiring the return of the patient.

An example of a system for automated classification for use with the present methods comprises an excitation source and a detector array, and optionally one or more filters designed to reduce the number of wavelengths to which the sample is exposed and/or which are observed from the sample, a means for comparing a result from the sample with a criterion, a means of attaching a positive designator to the sample, and a means of attaching a manipulation designator to the sample. The means for comparing the result can comprise an electronic device, which may be a computer, that can receive a signal from the detector array and compare it to a criterion, which may be a value stored in a memory, which can be a fixed memory or a dynamic memory and can be provided by hardware or software, or the value may be obtained by comparison to a signal obtained from a control sample. The means of attaching designators to the sample also can comprise electronic devices, which may be a computer, and can comprise a printer capable of marking the sample vial directly, or may print a label that is attached to the vial, or may designate the sample for manipulation electronically, for example by attaching a manipulation designator to a code, for example a barcode, already present on the vial, or by attaching a manipulation designator to a position in the device in which the sample is located. The term "attaching" encompasses a physical attachment to the sample and/or its vial, an electronic attachment to a representation of the sample and/or vial, or both. The means for comparing, means for attaching a positive designator, and means for attaching a manipulation designator may all be operated from a single electronic device such as a single computer.

An apparatus performing a method of the invention can be independent or can be integrated with additional components capable of performing further methods upon the sample. For example, the sample(s) can be further processed after its designation by an automated sample processor, and may be imaged by an automated imaging system. The automated classification system may be adapted to transfer the sample to an automated sample processor and/or imager, and can optionally be incorporated into such a system. Exemplary automated systems include Cytyc Corporation's ThinPrep® Imaging System, the TriPath FocalPoin™ Profiler, the ChromaVision Acis® System, the CompuCyt iCyte Imaging System, the Applied Imaging CytoVision™ System, and the Veracel Verasys Imaging System. The methods can be incorporated into sample processing devices such as those described in U.S. Pats. Nos. 5,185,084, 5,266,495, 6,010,909, 6,225,125, and 5,942,700, all assigned to Cytyc Corp.

The sample may be performed in conjunction with biochemical and/or molecular methods of analyzing the sample, for example methods of detecting a target species in the sample using a binding partner as a sensor molecule. Such methods may be performed in a format done in conjunction with the optical interrogation, or may be performed after separation of a portion of the sample. Such methods may analyze the sample for a target that may be any component of the sample that is desired to be detected.

Where the target is a cell or cell component or product, the cell can be of any origin, including prokaryotic, eukaryotic, or archea. The cell may be living or dead. If obtained from a multicellular organism, the cell may be of any cell type. The cell may be a cultured cell line or a primary isolate, the cell may be mammalian, amphibian, reptilian, plant, yeast, bacterial, spirochetal, or protozoan. The cell may be a normal cell, a mutated cell, a genetically manipulated cell, a tumor cell, etc. The target may be an infectious agent, a disease or infection marker, a protein, an antibody, an antigen, etc.

The sensor can be any substance which can selectively bind to its target when present in the sample. Nonlimiting examples of the sensor include a polynucleotide as described above, including a peptide nucleic acid and an aptamer, and an antibody as described above. Combinations of different sensors may also be used, which can allow for the detection and analysis of a plurality of targets in the sample. In one variation, the sensor may be a PNA that binds specifically to a target polynucleotide suspected of being present in the sample. Different labels may be used on different secondary sensors specific for different targets which allow for multiplex detection.

Sandwich techniques may be used to detect binding of the target to the sensor. For example, where the sensor is an antibody specific for a target, a second labeled antibody which does not interfere with the binding of the sensor antibody may be used to allow detection of binding of the target. Similarly, a polynucleotide that binds to a portion of the target or of the sensor:target complex without disrupting such complex can also be used. Labels useful for detecting a sensor:target complex include any substance which can be detected, directly or indirectly, in association with a target present in the sample upon binding of a sensor to the target. Exemplary labels include a chromophore, a lumiphore, a fluorophore, a chromogen, a hapten, an antigen, a radioactive isotope, a magnetic particle, a metal nanoparticle such as a gold or silver nanoparticle, an enzyme, and one member of a binding pair.

Although the invention has been described in some detail with reference to the preferred embodiments, those of skill in the art will realize, in light of the teachings herein, that certain changes and modifications can be made without departing from the spirit and scope of the invention. Accordingly, the invention is limited only by the claims.

What is claimed is:

1. An automated method of classifying a cytological sample, comprising:
   a) obtaining an initial cytological sample from a patient;
   b) providing the initial cytological sample in solution in a vessel;
   c) optically interrogating the solution containing the initial sample with at least one wavelength of light;
   d) determining, based on the interrogation, whether the solution containing the initial sample has an adequate concentration of cellular material;
   e) obtaining an additional cytological sample from the patient to be added to the solution if the solution containing the initial sample does not have an adequate concentration of cellular material;
   f) attaching a positive designator to the vessel if the solution containing the initial sample has an adequate concentration of cellular material and is satisfactory for preparing a specimen slide; and
   g) attaching a manipulation designator to the vessel if the solution containing the initial sample has an adequate concentration of cellular material but requires a manipulation to render the solution containing the initial sample satisfactory for slide preparation.

2. The method of claim 1, wherein the cellular material comprises prokaryotic, eukaryotic, or archea type cells.

3. The method of claim 1, wherein the positive designator indicates that the sample is satisfactory for automated slide preparation.

4. The method of claim 1, wherein the positive designator further indicates that the solution containing the initial sample is adequate in quantity to allow for withdrawal of a portion of the solution containing the initial sample prior to preparing the specimen slide.

5. The method of claim 1, wherein the manipulation to render the solution containing the initial sample satisfactory for slide preparation comprises adding acetic acid to the solution containing the initial sample.

6. The method of claim 1, wherein the manipulation to render the solution containing the initial sample satisfactory for slide preparation comprises adding a reducing agent to the solution containing the initial sample.

7. The method of claim 1, wherein the cellular material is endocervical cells.

8. The method of claim 1, wherein the solution containing the initial sample requires a manipulation to render the solution containing the initial sample satisfactory for slide preparation if a level of blood or mucus in the solution containing the initial sample exceeds a threshold level of blood or mucus.

9. The method of claim 1, wherein the positive designator comprises a physical marking on the vessel.

10. The method of claim 1, wherein the positive designator comprises a designation in an electronic memory.

11. The method of claim 1, wherein the manipulation designator comprises a physical marking on the vessel.

12. The method of claim 1, wherein the manipulation designator comprises a designation in an electronic memory.

13. The method of claim 1, wherein the initial sample is selected from the group consisting of blood; urine; semen; milk; sputum; mucus; plueral fluid; pelvic fluid; sinovial fluid; ascites fluid; a body cavity wash; eye brushing; skin scrapings; a buccal swab; a vaginal swab; a pap smear; a rectal swab; an aspirate; a needle biopsy; a section of tissue; plasma; serum; spinal fluid; lymph fluid; an external secretion of the skin, respiratory, intestinal, or genitourinary tract; tears; saliva; a tumor; an organ; a microbial culture; and an in vitro cell culture constituent.

14. The method of claim 1, wherein the solution comprises a water-soluble alcohol in an amount effective to preserve the sterility of the initial sample toward at least one contaminant.

15. The method of claim 1, wherein steps c) and d) occur in temporal conjunction with steps a) and b).

16. The method of claim 1, wherein step e) occurs in temporal conjunction with steps a) through d).

* * * * *